US010405737B2

(12) United States Patent
Tabata et al.

(10) Patent No.: US 10,405,737 B2
(45) Date of Patent: Sep. 10, 2019

(54) ENDOSCOPE LIGHT SOURCE APPARATUS

(71) Applicant: OLYMPUS CORPORATION, Tokyo (JP)

(72) Inventors: Motoki Tabata, Hino (JP); Takeshi Ito, Hino (JP); Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 290 days.

(21) Appl. No.: 15/380,081

(22) Filed: Dec. 15, 2016

(65) Prior Publication Data

US 2017/0095144 A1    Apr. 6, 2017

Related U.S. Application Data

(63) Continuation of application No. PCT/JP2015/064612, filed on May 21, 2015.

(30) Foreign Application Priority Data

Jun. 17, 2014   (JP) ................. 2014-124758

(51) Int. Cl.
*A61B 1/06* (2006.01)
*A61B 1/07* (2006.01)

(52) U.S. Cl.
CPC .......... *A61B 1/0684* (2013.01); *A61B 1/06* (2013.01); *A61B 1/0661* (2013.01); *A61B 1/07* (2013.01)

(58) Field of Classification Search
CPC ....... A61B 1/0661; A61B 1/06; A61B 1/0684; A61B 1/07; A61B 1/0669; G02B 23/2461

(Continued)

(56) References Cited

U.S. PATENT DOCUMENTS 5,971,576 A * 10/1999 Tomioka ............. G02B 6/0006
                                                                362/268
8,764,644 B2 * 7/2014 Kuroda ............. A61B 1/00096
                                                                359/385

(Continued)

FOREIGN PATENT DOCUMENTS

CN         102860809 A      1/2013
JP       2009-297311 A     12/2009

(Continued)

OTHER PUBLICATIONS

English translation of International Preliminary Report on Patentability dated Dec. 29, 2016 together with the Written Opinion received in related International Application No. PCT/JP2015/064612.

(Continued)

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

An endoscope light source apparatus includes a first light source section that emits first light, a second light source section that emits second light, and an optical path combiner that combines an optical path of the first light and an optical path of the second light. The etendue of the first light source section is smaller than the etendue of the second light source section. The optical path combiner has an optical deflection surface that deflects the second light, and has an aperture that allows the first light to pass through it within an area of the optical deflection surface. The optical path combiner deflects the second light so that a center axis of the optical path of the second light deflected by the optical deflection surface corresponds to a center axis of the optical path of the first light that has passed through the aperture.

8 Claims, 8 Drawing Sheets (58) Field of Classification Search
USPC .................................. 362/245, 574; 600/178
See application file for complete search history.

(56) References Cited

U.S. PATENT DOCUMENTS

| | | | |
|---|---|---|---|
| 9,115,862 B2* | 8/2015 | Morgenbrod | A61B 1/0653 |
| 2002/0022768 A1* | 2/2002 | Utsui | A61B 1/05 |
| | | | 600/178 |
| 2005/0013132 A1* | 1/2005 | Kim | H04N 9/3117 |
| | | | 362/231 |
| 2005/0288553 A1* | 12/2005 | Sugimoto | A61B 1/0005 |
| | | | 600/118 |
| 2009/0040754 A1* | 2/2009 | Brukilacchio | A61B 1/0653 |
| | | | 362/228 |
| 2010/0321772 A1* | 12/2010 | Reimer | A61B 1/043 |
| | | | 359/385 |
| 2011/0037948 A1* | 2/2011 | Horvath | A61B 1/0653 |
| | | | 351/221 |
| 2012/0013722 A1* | 1/2012 | Wong | A61B 1/00009 |
| | | | 348/66 |
| 2012/0182754 A1* | 7/2012 | Wolter | A61B 1/00167 |
| | | | 362/553 |
| 2012/0271111 A1* | 10/2012 | Namiki | G02B 21/16 |
| | | | 600/163 |
| 2014/0128743 A1* | 5/2014 | Yew | A61B 1/00163 |
| | | | 600/476 |
| 2014/0133011 A1* | 5/2014 | Schwedt | G02B 21/0032 |
| | | | 359/298 |
| 2015/0037750 A1* | 2/2015 | Moalem | A61B 5/0088 |
| | | | 433/29 |
| 2015/0099932 A1* | 4/2015 | Morimoto | H05B 33/0854 |
| | | | 600/180 |

FOREIGN PATENT DOCUMENTS

| | | | |
|---|---|---|---|
| JP | 2013-013560 A | | 1/2013 |
| JP | 2013013560 | * | 1/2013 |
| JP | 2013-039215 A | | 2/2013 |

OTHER PUBLICATIONS

International Search Report dated Aug. 11, 2015 issued in PCT/JP2015/064612.
Chinese Office Action dated May 16, 2018 in Chinese Patent Application No. 201580032382.9.
Chinese Office Action dated Jul. 27, 2017 in Chinese Patent Application No. 201580032382.9.
Chinese Office Action dated Feb. 20, 2019 in Chinese Patent Application No. 201580032382.9.

* cited by examiner

ENDOSCOPE LIGHT SOURCE APPARATUS

CROSS REFERENCE TO RELATED APPLICATIONS

This application is a Continuation Application of PCT Application No. PCT/JP2015/064612, filed May 21, 2015 and based upon and claiming the benefit of priority from Japanese Patent Application No. 2014-124758, filed Jun. 17, 2014, the entire contents of all of which are incorporated herein by reference.

BACKGROUND OF THE INVENTION

1. Field of the Invention

The present invention relates to an endoscope light source apparatus to which an endoscope is to be connected.

2. Description of the Related Art

In recent years, in endoscopy, besides normal light observation utilizing white light, specific light observation that improves visibility of a living body by utilizing light in a narrow wavelength band is being carried out. As a light source that generates the specific light, use of laser light has received attention because of, in particular, its high narrow-band properties, and specific light of various combinations is being developed. Jpn. Pat. Appln. KOKAI Publication No. 2013-013560 discloses, as an example, a constitution that combines the optical path of laser light with the optical path of white light by a reflecting plate to reflect laser light arranged in the optical path of white light in order to enable observation of oxygen saturation of a surface blood vessel. This constitution enables even conventionally-used endoscopes to use novel specific light. In general, in conventional endoscopes, light is guided to the distal end by a bundle fiber, and emitted as illumination light after light distribution is adjusted by a lens, etc.

In contrast, an endoscope that uses laser light sources, not a conventional light source such as a lamp or light emitting diodes, even in normal observation, has been developed in recent years. Such an endoscope can produce white light or any specific light by combinations enabled by using a single optical fiber as a light guide and exciting a phosphor mounted on a distal end portion of the endoscope, and can perform normal observation and specific light observation only by the laser light sources. In the endoscope using a single optical fiber, since the fiber is the single optical fiber, a smaller diameter of the endoscope can be provided and a lower-power endoscope system can be also achieved.

BRIEF SUMMARY OF THE INVENTION

The present invention is directed to an endoscope light source apparatus to which an endoscope is to be connected. The endoscope light source apparatus includes a first light source section including a first light source that emits first light source light, a second light source section including a second light source that emits second light source light, and an optical path combiner that combines an optical path of the first light source light and an optical path of the second light source light. The etendue of the first light source section is smaller the etendue of the second light source section. The optical path combiner has an optical deflection surface that deflects the second light source light, and has an aperture that allows the first light source light to pass through the aperture within an area of the optical deflection surface. The optical path combiner deflects the second light source light so that a center axis of the optical path of the second light source light deflected by the optical deflection surface corresponds to a center axis of the optical path of the first light source light that has passed through the aperture. The first light source light and the second light source light entering the endoscope through the respective optical paths whose center axes correspond to each other.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of the present invention will be described with reference to the drawings.

First Embodiment

Constitution

Figure 1:
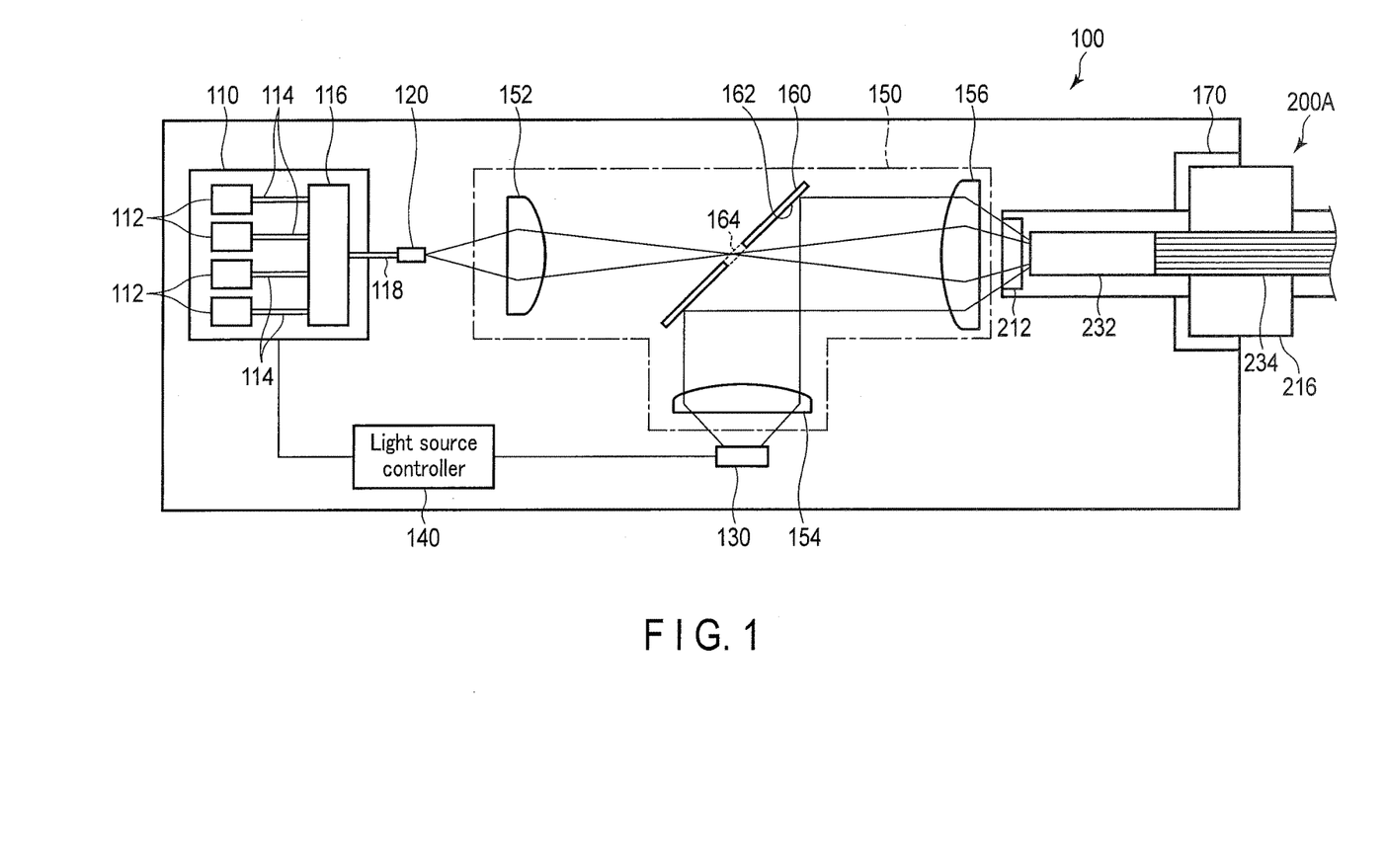
FIG. 1 shows a first embodiment of an endoscope light source apparatus.

FIG. 1 shows a first embodiment of an endoscope light source apparatus.

The endoscope light source apparatus 100 of the present embodiment includes a laser light source section 110 as a first light source section including a first light source that emits first light source light, an LED light source section 130 as a second light source section including a second light source that emits second light source light, a light source controller 140 that controls the laser light source section 110 and the LED light source section 130, a scope connector 170 connectable to any endoscope, and a light guiding optical system 150 that guides the first light source light emitted from the laser light source section 110 and the second light source light emitted from the LED light source section 130 to the endoscope connected to the scope connector 170.

The laser light source section 110 includes laser light sources 112 of different light emission wavelengths. The laser light sources 112 include laser diodes (LDs) having emission light wavelengths of 405 nm, 445 nm, and 515 nm, for example. The laser light source section 110 also includes optical fibers 114 that guide laser light emitted from the laser light sources 112, an optical combiner 116 that combines laser light guided by the optical fibers 114, an optical fiber 118 that guides laser light combined by the optical combiner 116, and a laser light emitting portion 120 that emits laser light guided by the optical fiber 118 to space.

In the laser light source section 110 accordingly constituted, the laser light sources 112 are optically connected to the optical fibers 114, and laser light guided by the optical fibers 114 is combined by the optical combiner 116 into the optical fiber 118, and guided to the laser light emitting portion 120. The laser light emitting portion 120 is constituted by the optical fiber 118 optically connected to the optical combiner 116 and a member that holds the optical fiber 118, and is capable of emitting laser light from the distal end of the optical fiber 118 into a space with a constant divergence angle. The distal end of the optical fiber 118 may be, for example, surface-polished, but may also be lens-finished for control of the divergence angle of exit light.

The LED light source section 130 comprises a light source capable of emitting white light having broad wavelength components in the visible light range. For example, the LED light source section 130 includes a LED light source capable of emitting white light. The LED light source section 130 can emit LED light to space with a constant divergence angle.

The etendue of the laser light source section 110 is smaller than the etendue of the LED light source section 130.

The laser light source section 110 and the LED light source section 130 are controlled by the light source controller 140. The light source controller 140 can separately control the on/off operation and exit light quantity of the laser light sources 112 of the laser light source section 110. The light source controller 140 can also control the on/off operation and exit light quantity of the LED light source section 130.

To the scope connector 170, one of various types of endoscopes selected in accordance with the intended purpose can be connected. To the scope connector 170, a bundle fiber scope 200A shown in FIG. 4 and described later, or a single fiber scope 200B shown in FIG. 5 and described later may be connected, for example. FIG. 1 shows a state where an endoscope that is a bundle fiber scope 200A is connected to the scope connector 170.

The light guiding optical system 150 includes a lens 152 for lasers that is light converger that transforms divergent light emitted from the laser light source section 110 into convergent light, an lens 154 LED that is collimator that transforms divergent light emitted from the LED light source section 130 into a generally parallel beam, an optical path combiner 160 that combines the optical path of laser light emitted from the laser light source section 110 and the optical path of LED light emitted from the LED light source section 130, and a scope connection lens 156 that couples laser light and/or LED light that has passed through the optical path combiner 160 to the endoscope connected to the scope connector 170.

The lens 152 for lasers and the scope connection lens 156 are arranged so that the optical axes (optical center axes) of the both correspond to each other, and constitute an optical system that guides laser light. The laser light emitting portion 120 is arranged so that its optical axis (center axis of the beam of exit light) corresponds to an optical axis of the optical system constituted by the lens 152 for lasers and the scope connection lens 156.

The distal end of the optical fiber 118 of the laser light source section 110 is usually as microscopic as 50 to 300 μm, and may cause burning, etc. of a foreign object by energy concentration of exit laser light. Accordingly, the space between the laser light emitting portion 120 and the lens 152 for lasers is preferably covered with and sealed by a holding member, although it is not shown in FIG. 1.

The optical path combiner 160 includes an optical deflection surface that deflects LED light, which is the second light source light, such as a reflecting surface 162. The optical path combiner 160 also has an aperture 164 that allows laser light, which is the first light source light, to pass within an area of the reflecting surface 162.

The LED light source section 130 is arranged so that, for example, the center axis of the optical path of the LED exit light forms an angle of 90° with respect to the center axis of the optical path of the laser exit light of the laser light source section 110. The optical path combiner 160 is arranged so that the reflecting surface 162 forms an angle of 45° with respect to each of the center axis of the optical path of the laser exit light and the center axis of the optical path of the LED exit light. In other words, the optical path combiner 160 is tilted 45° with respect to the optical axis of the optical system constituted by the lens 152 for lasers and the scope connection lens 156. In addition, the optical path combiner 160 is arranged so that the center of the aperture 164 is positioned on the center axis of the optical path of laser light, and the aperture 164 is positioned on or in the vicinity of a light convergence point of laser light transformed into convergent light along the optical path of laser light. The LED light source section 130 is arranged so that the center axis of the optical path of the LED exit light corresponds to the center of the optical path combiner 160. With such an arrangement, the optical path combiner 160 deflects or reflects LED light so that the center axis of the optical path of LED light deflected or reflected by the light deflecting or reflecting surface corresponds to the center axis of the optical path of laser light that has passed the aperture 164.

This constitution enables combining the optical path of laser light and the optical path of LED light so that the center axes thereof correspond to each other.

Laser light emitted from the laser light source section 110 is converged inside the aperture 164 of the optical path combiner 160 by the lens 152 for lasers, so as to pass through the optical path combiner 160, and then becomes divergent light and heads for the scope connection lens 156. From the laser light source section 110 to the scope connection lens 156, the optical path of laser light is never bent.

LED light emitted from the LED light source section 130 is transformed into a parallel beam by the lens 154 LED, and then reflected by the reflecting surface 162 of the optical path combiner 160, and heads for the scope connection lens 156.

The center axis of the optical path of LED light corresponds to the center axis of the optical path of laser light between the optical path combiner 160 and the scope connection lens 156. Accordingly, the optical path of laser light extends straight without being bent, whereas the optical path of LED light is bent by the optical combiner 160 so that the center axis of LED light corresponds to the center axis of the optical path of laser light.

The laser light and LED light heading for the scope connection lens 156 are converged by the scope connection lens 156, and enters the endoscope connected to the scope connector 170. Namely, the laser light and LED light that have passed the optical path combiner 160 pass through the respective optical paths having the center axes that correspond to each other and enter the endoscope (e.g., a bundle fiber scope 200A) connected to the scope connector 170.

The LED light that enters the aperture 164 of the optical path combiner 160 is not reflected and is lost; however, the area of the aperture 164 of the optical path combiner 160 can be made so small as to have substantially no influence.

Figure 2:
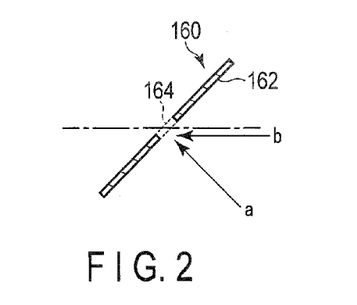
FIG. 2 is a cross-sectional side view of the optical path combiner shown in FIG. 1.
Figure 3:
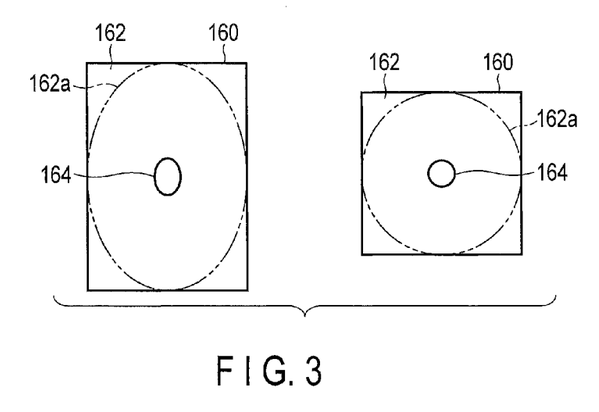
FIG. 3 shows on the left side the optical path combiner viewed in the direction of arrow a shown in FIG. 2, and shows on the right side the optical path combiner viewed in the direction of arrow b shown in FIG. 2.

Referring to FIGS. 2 and 3, the details of the optical path combiner 160 will be described. FIG. 2 is a cross-sectional side view of the optical path combiner 160, and FIG. 3 shows on the left side the optical path combiner 160 viewed in the direction of arrow a shown in FIG. 2, and shows on the right side the optical path combiner 160 viewed in the direction of arrow b shown in FIG. 2.

As mentioned above, the optical path combiner 160 has the reflecting surface 162 capable of reflecting white light and, within the area of the reflecting surface 162, the aperture 164 that allows laser light to pass. The reflecting surface 162 may have any area sufficient to reflect LED light. For example, the reflecting surface 162 is provided on the entire surface of the optical path combiner 160 except for the aperture 164, and the optical path combiner 160 may be a rectangle larger than the beam spot of LED light for easy mounting.

The shape of the aperture 164 is preferably almost the same as the beam shape of laser light as projected onto a plane perpendicular to the center axis of the optical path of laser light in order to ensure the maximum area of the reflecting surface 162. The beam shape indicates a beam area where the beam has a certain light quantity ratio with respect to the peak light quantity, such as not less than $1/e^2$, in the light intensity distribution of the case where laser light is viewed in the direction of its optical path (direction indicated by arrow b in FIG. 2). For example, when the beam shape is circular, the shape of the aperture 164 is preferably circular as projected onto a plane perpendicular to the center axis of the optical path of laser light, and thus is preferably oval as viewed in the direction perpendicular to the reflecting surface 162 of the optical path combiner 160 (direction indicated by arrow a in FIG. 2). In the present embodiment, since the optical path combiner 160 is tilted 45° with respect to the optical axis, the shape of the aperture 164 can be circular as projected onto a plane perpendicular to the center axis of the optical path of laser light by making the shape an oval $1/\sin 45° = 2^{1/2}$ times depressed in the direction of the center axis of the optical path of laser light projected onto the reflecting surface 162 as viewed from the direction perpendicular to the reflecting surface 162 of the optical path combiner 160 (direction indicated by arrow a in FIG. 2).

The size of the aperture 164 needs to be larger than at least the light convergence diameter of laser light when the aperture 164 is projected onto a plane perpendicular to the center axis of the optical path of laser light so as to allow laser light to pass. The light convergence diameter of laser light is restricted by the law of constant etendue (when assuming that the etendue is E, the area is S, and the radial solid angle of light is $\pi NA^2$ in the optical system, $$E = \pi \cdot S \cdot NA^2 \qquad (1)$$

is constant), and has a constant size. Specifically, when assuming that the area of the exit end of the optical fiber 118 at the laser light emitting portion 120 is $S_1$, the exit angle is $\theta_1$, $NA_1$ is $\sin \theta_1$, the area of the aperture 164 is $S_2$, the entrance angle to the aperture 164 is $\theta_2$, and $NA_2$ is $\sin \theta_2$, it is preferable that the relationship $$S_2 \geq S_1 \cdot (NA_1^2 / NA_2^2) \qquad (2)$$

is satisfied.

For the same reason as the above-described reason, the outline 162a of the irradiation area of LED light formed on the reflecting surface 162 of the optical path combiner 160 is oval as viewed in the direction perpendicular to the reflecting surface 162 of the optical path combiner 160 (direction indicated by arrow a in FIG. 2), and is circular as viewed in the direction of the center axis of the optical path of laser light (direction indicated by arrow b in FIG. 2).

The endoscope light source apparatus 100 of the present embodiment can be used for scopes having different optical characteristics.

Figure 4:
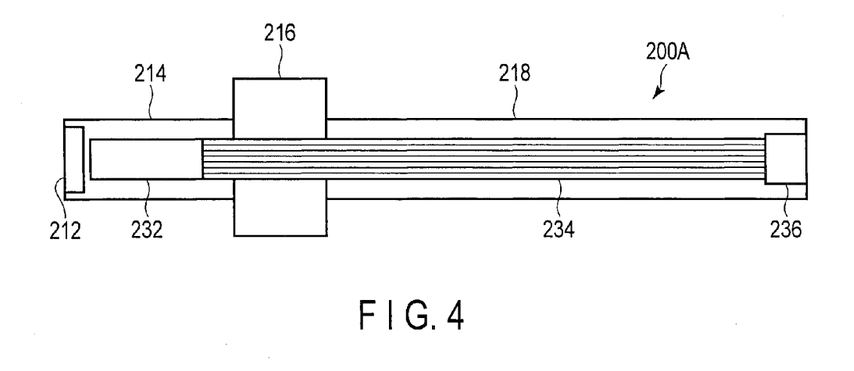
FIG. 4 shows a schematic constitution of an illumination system of a bundle fiber scope.

FIG. 4 shows a schematic constitution of an illumination system of a bundle fiber scope 200A, an endoscope utilizing a bundle fiber, which includes bundled optical fibers, as a light guide, as an example.

The bundle fiber scope 200A includes an optical connecting section 214 to be inserted in the endoscope light source apparatus 100, a scope connector section 216 to be connected to the scope connector 170 of the endoscope light source apparatus 100, and a flexible section 218. The optical connecting section 214 is provided with a cover glass 212, which is a light entrance section that takes in light (laser light and/or LED light) from the light guiding optical system 150 of the endoscope light source apparatus 100. The optical connecting section 214 also includes a rod lens 232 arranged in the optical connecting section 214 to receive light that has entered the cover glass 212, a bundle fiber 234, which is a light guide, optically connected to the rod lens 232, and an optical characteristic converter 236 (e.g., a lens group) arranged at a distal end portion of the flexible section 218. The bundle fiber 234 extends in the flexible section 218 over almost the entire length of the flexible section 218, and is optically connected to the optical characteristic converter 236.

The bundle fiber scope 200A is connected to the endoscope light source apparatus 100 by engagement of the scope connector section 216 with the scope connector 170 of the endoscope light source apparatus 100. In this state, the center axis of the optical path of the laser light and the center axis of the optical path of the LED light correspond to the optical axis of the entrance end of the bundle fiber scope 200A. In other words, the endoscope light source apparatus 100 and the bundle fiber scope 200A are designed to be accordingly arranged when the bundle fiber scope 200A is connected to the endoscope light source apparatus 100.

The optical axis of the entrance end is intended to be the optical axis (optical center axis) of an optical element in the endoscope that is arranged closest to the scope connection lens 156 in the endoscope light source apparatus 100, except for an element that does not substantially influence the optical characteristics, such as the cover glass 212. In this case, the optical axis of the entrance end corresponds to the optical axis of the rod lens 232.

The entrance light (laser light and/or LED light) from the endoscope light source apparatus 100 enters the cover glass, which is the light entrance section, and then is made uniform in intensity by being reflected multiple times in the rod lens 232 and guided to the bundle fiber 234. The entrance light is then guided by the bundle fiber 234 to the lens group, which is the optical characteristics converter 236, arranged at the distal end portion of the flexible section 218, and is emitted as illumination light after exit light distribution is widened by the lens group.

This type of endoscope apparatus (the endoscope light source apparatus 100 and the bundle fiber scope 200A) can use LED light as white light observation light, and laser light as special observation light by switching. Narrow Band Imaging (NBI) specific light observation, which highlights blood vessels of the mucous surface, is enabled by applying, as specific light, laser light of the wavelengths of 415 nm and 515 nm that can easily be absorbed by blood hemoglobin, for example. The combination of laser light is not limited to this, and various specific light may be generated by various combinations of wavelengths.

Figure 5:
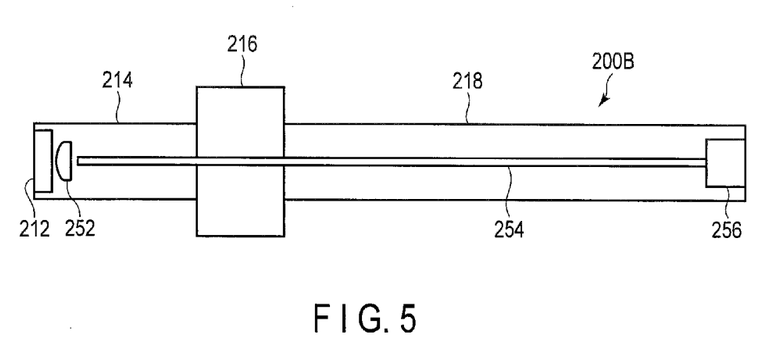
FIG. 5 shows a schematic constitution of an illumination system of a single fiber scope.
Figure 6:
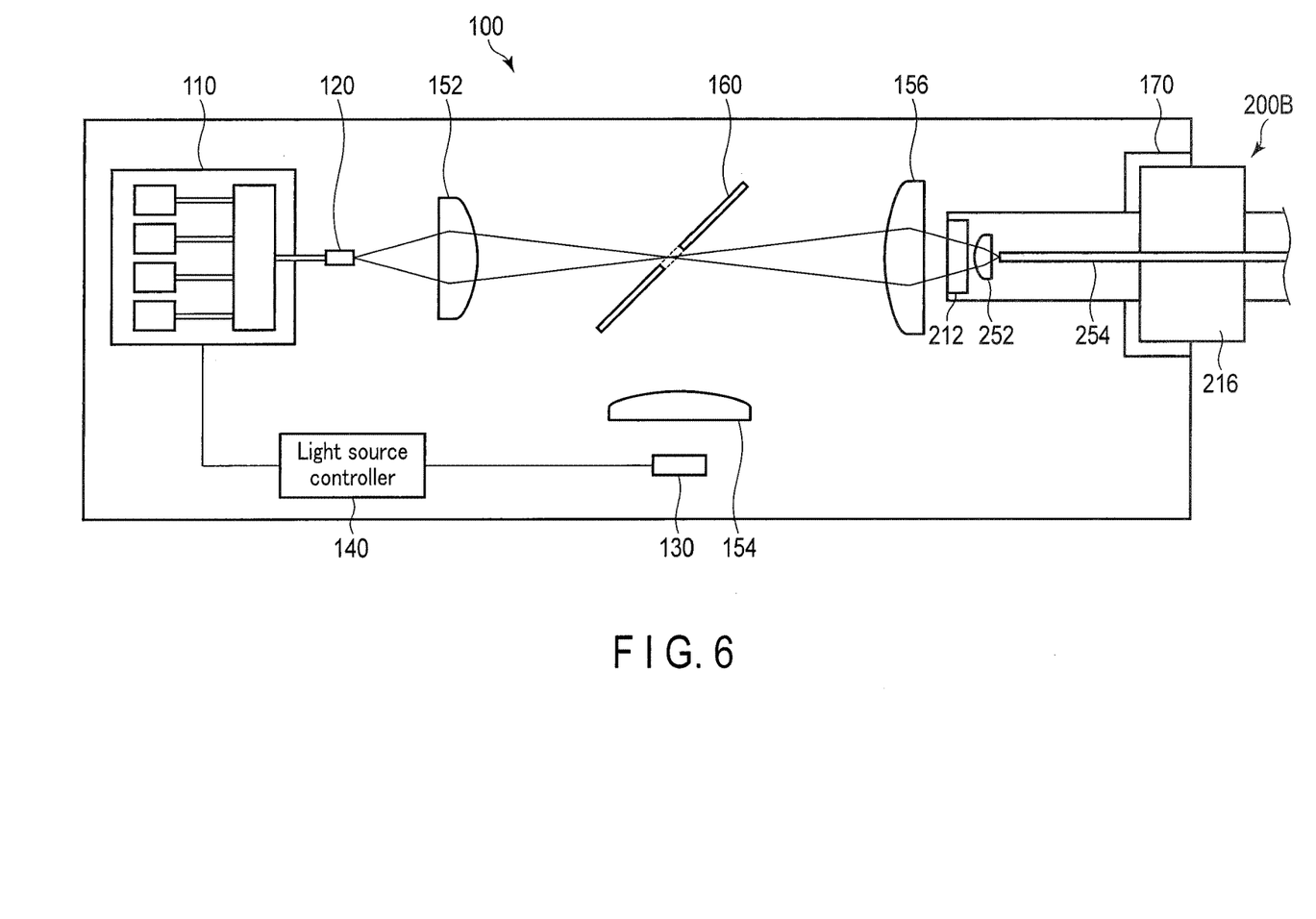
FIG. 6 shows the endoscope light source apparatus to which the single fiber scope shown in FIG. 5 is connected.

FIG. 5 shows a schematic constitution of an illumination system of a single fiber scope 200B, an endoscope utilizing a single optical fiber, as another example. FIG. 6 shows a state where the single fiber scope 200B is connected to the endoscope light source apparatus 100.

Like the bundle fiber scope 200A, the single fiber scope 200B includes an optical connecting section 214, a scope connector section 216, and a flexible section 218. The constitutions of those elements are the same as those of the bundle fiber scope 200A. The single fiber scope 200B is different in the inner optical system from the bundle fiber scope 200A. The single fiber scope 200B also includes a fiber connection lens 252 arranged in the optical connecting section 214 to receive light that has entered the cover glass 212, a single optical fiber 254, which is a light guide, optically connected to the fiber connection lens 252, and an optical characteristics converter 256 (e.g., a phosphor unit) arranged at a distal end portion of the flexible section 218. The single optical fiber 254 extends in the flexible section 218 over almost the entire length of the flexible section 218, and is optically connected to the optical characteristics converter 256.

The single fiber scope 200B is connected to the endoscope light source apparatus 100 in the same manner as the bundle fiber scope 200A. In this state, the center axis of the optical path of laser light and the center axis of the optical path of LED light correspond to the optical axis of the entrance end of the single fiber scope 200B. In this case, the optical axis of the entrance end corresponds to the optical axis of the fiber connection lens 252.

The entrance light (laser light and/or LED light) from the endoscope light source apparatus 100 enters the cover glass 212, which is the light entrance section, and is converged by the fiber connection lens 252 and optically coupled to the entrance end of the single optical fiber 254. The entrance light is then guided by the single optical fiber 254 to the phosphor unit, which is the optical characteristics converter 256, arranged at the distal end portion of the flexible section 218. The phosphor unit includes at least one type of phosphor, and is a unit capable of changing the wavelength of the entrance light and then emitting it as illumination light after. The phosphor unit is provided with, for example, YAG that emits yellow light under excitation by blue light, β sialon that emits green light under excitation by blue-violet light, and a light diffusion member for diffusing fluorescence and some transmitted laser light to mix them. This combination enables generation of white light including a blue component and a yellow component by exciting a YAG phosphor by laser light with the wavelength of 445 nm, and generation of NBI specific light including a blue-violet component and a green component by exciting a β sialon phosphor by laser light with the wavelength of 415 nm.

This type of endoscope apparatus (the endoscope light source apparatus 100 and the single fiber scope 200B) can generate white light and specific light by combinations of a type of phosphor included in the phosphor unit, which is the optical characteristics converter 256, and a wavelength of laser light applied to the phosphor unit, so that it is not necessary to cause LED light to enter the single fiber scope 200B from the endoscope light source apparatus 100, and only laser light is caused to enter.

Advantage

The present embodiment can improve the optical coupling efficiency to endoscopes under great design flexibility.

For example, the conventional constitution as described in Jpn. Pat. Appln. KOKAI Publication No. 2013-013560 in which laser light is combined with the optical path of white light has difficulty in increasing the optical coupling efficiency to the single fiber scope 200B as shown in FIG. 5. Specifically, since the core diameter of the single optical fiber 254 is as microscopic as approximately 50 to 300 μm, the positions of the optical members must be precisely adjusted and then mounted in order to couple laser light to it.

However, the conventional constitution requires positioning of the angle of the reflecting plate in addition to the positions of the light emitting section and the single fiber scope. In particular, misalignment of the angle of the reflecting plate misaligns the optical axis after reflection by twice the angle misalignment of the reflecting plate, and has a great influence on the coupling efficiency. Therefore, it is actually difficult to improve the coupling efficiency. Even if a light source apparatus is intended to have compatibility with a single fiber scope, the light source apparatus needs to be designed with a great restriction on the usage efficiency of light. Therefore, a dedicated light source apparatus needs to be prepared for full use of the function of the single fiber scope.

In contrast, the constitution of the present embodiment can improve the coupling efficiency to the single fiber scope 200B, which requires precise adjustment because the optical axis of the optical system from the laser light emitting portion 120 to the entrance end of the endoscope, i.e., the center axis of the optical path of laser light, is straight, and no reflecting member exists therebetween, which facilitates the adjustment of laser light. Consequently, the securing of connection compatibility from the common connection end (scope connector 170) to the single fiber scope 200B and the bundle fiber scope 200A, which has been difficult so far, is enabled. The optical path combiner 160, which is a reflecting member, exists on the optical path of LED light. However, the entrance aperture of the bundle fiber scope required by LED light is 1.5 to 4 mm, which is larger than that of the single fiber, and the influence of misalignment is extremely small and causes no substantial problem in comparison to the connection to the single fiber.

The aperture 164 of the optical path combiner 160 may be constituted by a transparent member, which also enables a smaller adjustment error than the adjustment of the reflecting member. However, when light is transmitted through a flat transparent member tilted with respect to the center axis of the optical path of laser light, a slight misalignment of the optical path is caused (the optical path is slightly shifted) due to a difference in refractive index. Therefore, use of the aperture is more efficient.

The conventional constitution also has a problem related to the loss caused when combining LED light. In the conventional constitution, the reflecting plate exists in the optical path, and light is shaded thereby and is lost. This causes a decrease in the optical coupling efficiency. The decrease in the optical coupling efficiency can be inhibited by making the reflecting area smaller; however, if thin laser light is reflected by a smaller reflecting plate, the energy density of laser light on the reflecting surface becomes extremely high. As a result, a problem of reliability such as burning a foreign object attached to the reflecting surface is caused. Therefore, the reflecting area of a certain size needs to be assured, and a decrease in the optical coupling efficiency to some extent is unavoidable.

The constitution of the present embodiment allows laser light to pass through the aperture 164 of the optical path combiner 160, and thus does not cause energy concentration on any member. Without the problem of the burning of a foreign object, the size of the aperture 164 can be reduced. Laser light has low etendue in general, and can converge to a very small diameter. Therefore, the aperture 164 can be made very small. Let us assume the optical system in which the core diameter of the exit fiber is 100 μm, the exit NA is 0.2, and laser light is transformed into convergent light of NA=0.05 by the lens 152 for lasers. According to formula (2), the flux diameter at the aperture 164 is 400 μm. Even in consideration of misalignment in mounting, preparation of an aperture having the diameter of, for example, approximately 1 mm as projected onto a plane perpendicular to the center axis of the optical path of laser light, sufficiently allows the laser light to pass. In this case, if the diameter of the reflecting surface 162 is 20 mm when the reflecting surface 162 is projected onto a plane perpendicular to the center axis of the optical path of laser light, the aperture 164 has the size having the area ratio of 0.25% with respect to the reflecting surface 162, and the loss caused by the aperture 164 can be kept down to a minuscule quantity. The area of the aperture 164 can be set with high flexibility in accordance with the design of the optical system and mounting. For example, if the diameter of the aperture 164 is increased to 4 mm to further increase the mounting tolerance, the area ratio relative to the reflecting surface 162 having the diameter of 20 mm is 4%, which does not cause any big problem in practical use. The size of the aperture 164 is not limited to the above example, and the aperture 164 may be designed in consideration of the balance of required efficiency. For the above-described reason, even in consideration of the loss of LED light at the optical path combiner 160, it is useful to coaxially arrange the laser light emitting portion 120 of the laser light source section 110 having low etendue as an extension of the center axis of the combined optical path.

Jpn. Pat. Appln. KOKAI Publication No. 2013-013560 also discloses that a reflecting plate is a dichroic mirror that reflects light of laser light wavelength band components and transmits light of the other white light wavelength band components. However, when light of visible wavelength band components is used as laser light, since the light of the laser light wavelength band is lost from the white light, this constitution causes a problem that the color of the white light illumination changes.

In the present embodiment, such a loss of light of a specific wavelength band from white light is not caused, and illumination color is uninfluenced. This advantage improves efficiency in optical characteristics of LED light, prevents light of a specific wavelength band from being lost, and facilitates realization of any illumination light characteristics in design.

Figure 7:
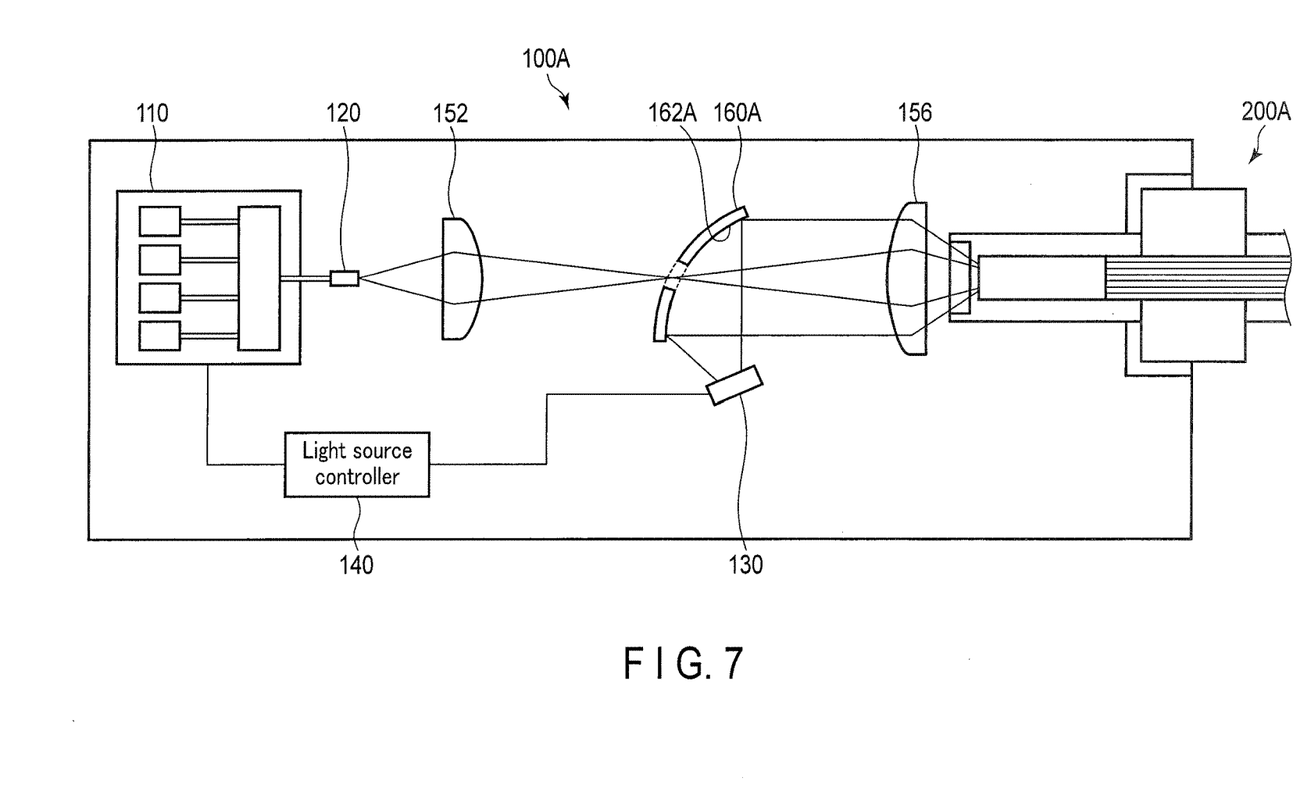
FIG. 7 shows an endoscope light source apparatus including an optical path combiner having a concave reflecting surface.

In addition, the present embodiment enables flexible design of the optical path combiner. For example, as shown in FIG. 7, an optical path combiner 160A having a concave reflecting surface 162A may be arranged instead of the optical combiner 160 having the flat reflecting surface 162. In this endoscope light source apparatus 100A, since the concave reflecting surface 162A has functions of reflecting and converging white light, the lens for LED is omitted. This contributes to reduction in size of the apparatus. The shape of the reflecting surface is not limited to this example, and flexibly designed, which can provide the optical path combiner with any optical function, such as convergence and divergence of LED light, intensity distribution control, or combination of LED light, without influencing laser light, and can improve flexibility in optical system design.

Those advantages enable improvement in flexibility and easiness in optical design of LED light while ensuring the optical coupling efficiency of laser light to the single fiber. Accordingly, an endoscope light source apparatus that facilitates realization of connection compatibility with a single fiber scope and has improved optical connection characteristics with respect to the conventional bundle fiber scope can be provided.

Modifications

For improvement of the optical coupling efficiency, it is desirable to make the optical axis of the optical system from the laser light emitting portion 120 to the light guide in the endoscope straight when the endoscope is connected. However, the constitution is not necessarily limited thereto. For example, the optical axis of the scope connection lens 156 in the endoscope light source apparatus 100 may be tilted on purpose with respect to the optical axis of the entrance end of the endoscope to allow laser light to enter the light guide of the endoscope at an angle so as to adjust the exit light distribution from the endoscope distal end.

The angle of the center axis of the optical path of LED light toward the optical path combiner 160 with respect to the center axis of the optical path of laser light need not necessarily be 90°, and may be changed at will. In accordance with the change, the arrangement angle of the optical path combiner 160 with respect to the center axis of the optical path of laser light and the shape and size of the aperture 164 should be adjusted.

LED light that enters the optical path combiner 160 need not be a parallel beam, and may have a divergence angle equivalent to that of the laser light after passing the aperture 164, for example. In this case, the position of the light convergence point of laser light is easily caused to correspond to that of LED light in the endoscope, making the connection position of the endoscope easy to design.

The laser light source 112 in the laser light source section 110 is not limited to the laser diode. In addition, the light source in the LED light source section 130 is not limited to the LED light source, and the LED light source section 130 may have a lamp light source, such as a xenon lamp, instead of the LED light source.

Figure 8:
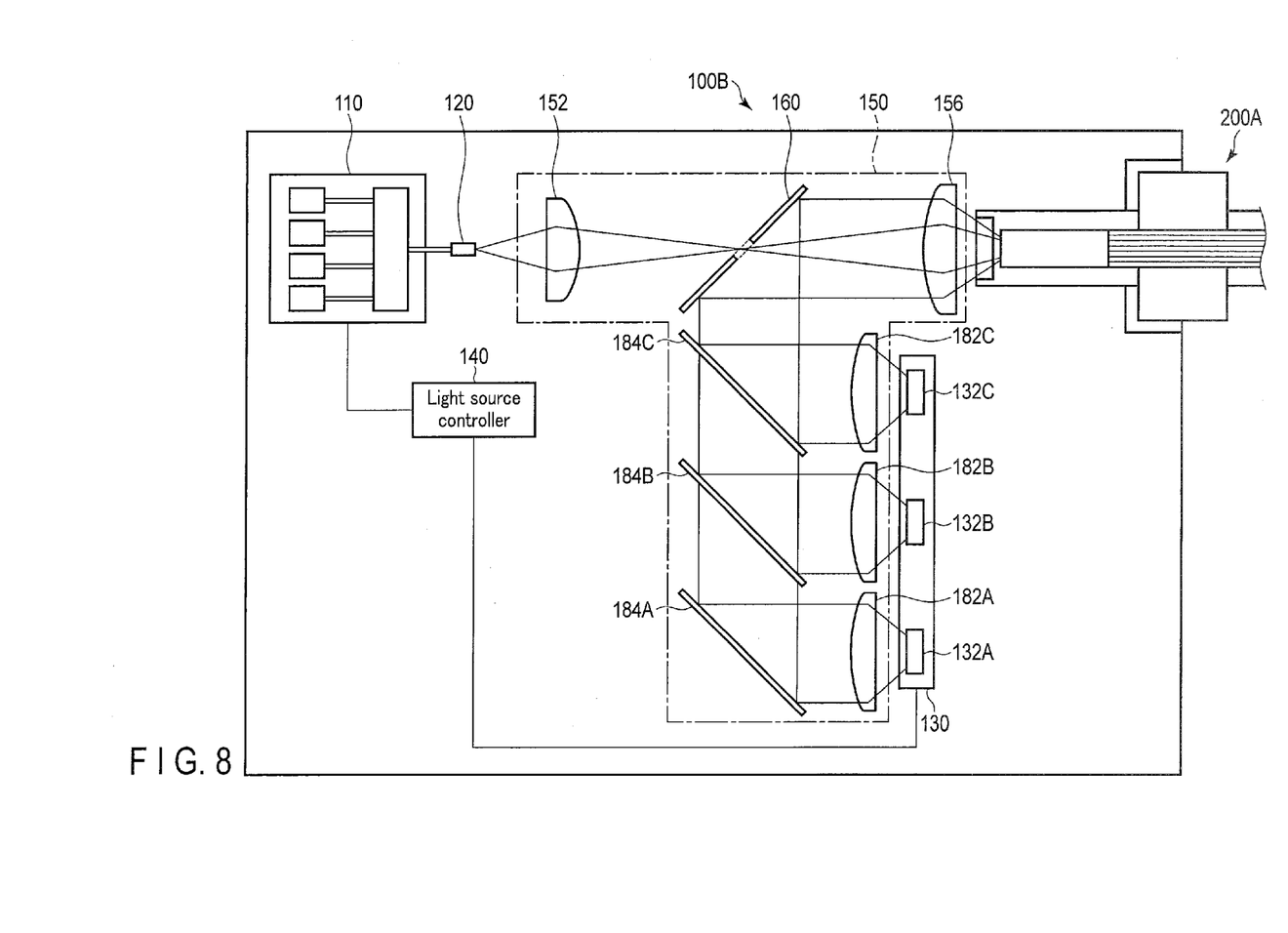
FIG. 8 shows an endoscope light source apparatus including a LED light source section including LED light sources that emit red light, green light, and blue light, respectively.

The LED light source section 130 need not necessarily have a white LED light source, and may have LED light sources 132A, 132B, and 1320 that emit red light, green light, and blue light, respectively, which are combined later to become white light, as shown in FIG. 8, for example. In this endoscope light source apparatus 100B, the light guiding optical system 150 includes lenses 182A, 182B, and 182C for LED, which are collimator that transforms divergent light emitted from LED light sources 132A, 132B, and 132C into generally parallel beams, and reflecting/transmitting elements 184A, 184B, and 184C for combining light from the lenses 182A, 182B, and 182C for LED. For example, reflecting/transmitting element 184A has a function of reflecting red light, reflecting/transmitting element 184B has a function of transmitting red light and reflecting green light, and reflecting/transmitting element 184C has a function of transmitting red and green light and reflecting blue light. Red light, green light, and blue light emitted from the LED light sources 132A, 132B, and 132C are combined by the reflecting/transmitting elements 184A, 184B, and 184C to become white light.

Second Embodiment

Constitution

Figure 9:
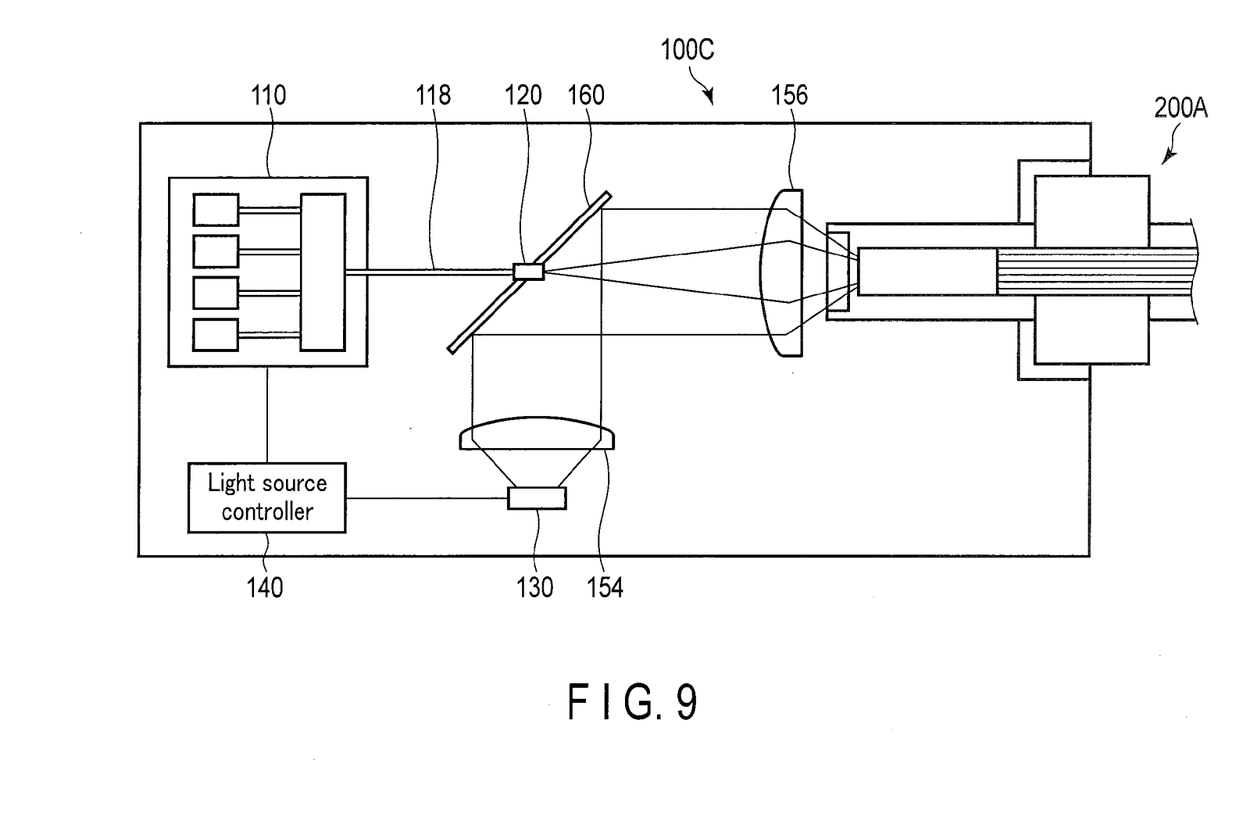
FIG. 9 shows a second embodiment of an endoscope light source apparatus.
Figure 10:
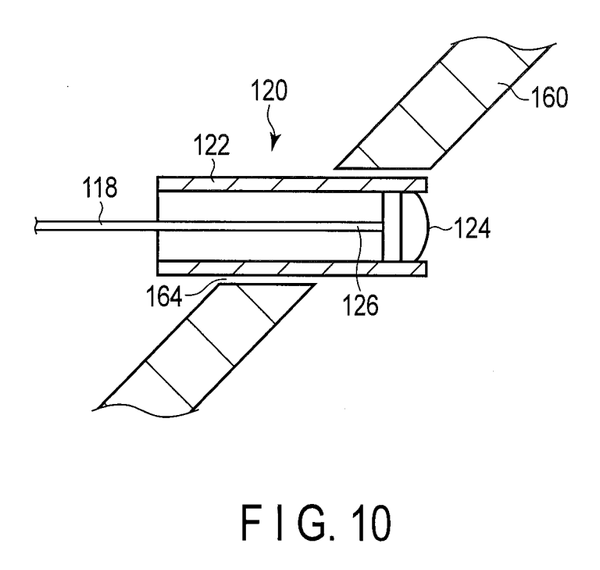
FIG. 10 shows a cross-section of a laser light emitting portion and an optical path combiner shown in FIG. 9.

FIG. 9 shows a second embodiment of an endoscope light source apparatus. In FIG. 9, the same members as those shown in FIG. 1 are assigned with the same reference numerals as those shown in FIG. 1, and detailed descriptions thereof are omitted. The following descriptions will be provided while placing importance on the parts different from those in FIG. 1. Namely, the members etc. not described below are the same as those in the first embodiment. FIG. 10 shows a cross-section of a laser light emitting portion 120 and an optical path combiner 160 shown in FIG. 9.

In the endoscope light source apparatus 100C of the present embodiment, the laser light emitting portion 120 is arranged so as to penetrate the aperture 164 of the optical path combiner 160 as shown in FIG. 9. The laser light emitting portion 120 includes a fixing member 122 that fixes the optical fiber 118, and the lens 124 for lasers for controlling the divergence angle of laser light emitted from the optical fiber 118. The exit end 126 of the optical fiber 118 is arranged in the vicinity of the aperture 164 of the optical path combiner 160 along the optical path of laser light. Therefore, laser light is emitted from a position in the vicinity of the aperture 164.

Laser light is guided by the optical fiber 118, and emitted from the exit end 126 of the optical fiber 118 as diffusion light. The emitted laser light is subjected to adjustment of the divergence angle by the lens 124 for lasers, and then converged by the scope connection lens 156 and enters the endoscope.

As in the first embodiment, LED light may be reflected by the reflecting surface 162 except for the aperture 164 of the optical path combiner 160 and be combined with the same optical path as laser light.

Advantage

In the present embodiment, the laser light emitting portion 120 can be arranged closer to the endoscope than in the first embodiment. In general, as the distance between the laser light emitting portion 120 and the endoscope increases, mechanical position misalignment is more likely to occur, and the light beam position misalignment on the endoscope side increases due to the misalignment of the optical axis angle. Therefore, the present embodiment can further improve the optical coupling efficiency of laser light to the single fiber scope.

Modifications

The laser light emitting portion 120 need not necessarily be arranged at almost the same position as the optical path combiner 160. For example, the optical fiber 118 may extend to penetrate the aperture 164 of the optical path combiner 160, and the laser light emitting portion 120 may be arranged closer to the endoscope than the optical path combiner 160. In this case, laser light is emitted from a position closer to the endoscope than to the optical path combiner 160.

While certain embodiments of the present invention have been described with reference to the drawings, the present invention is not limited to them and may be modified or altered without departing from the spirit of the invention. The modification or alteration mentioned herein includes proper combinations of the aforesaid embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope light source apparatus to which an endoscope is to be connected, the endoscope light source apparatus comprising:
   a first light source section including a first light source that emits first light source light;
   a second light source section including a second light source that emits second light source light; and
   an optical path combiner that combines an optical path of the first light source light and an optical path of the second light source light,
   a light converger that transforms the first light source light emitted from the first light source section into convergent light,
   an etendue of the first light source section being smaller than an etendue of the second light source section,
   the optical path combiner having an optical deflection surface that deflects the second light source light, and having an aperture within an area of the optical deflection surface, the aperture being positioned at a distance from the light converger,
   the optical path combiner deflecting the second light source light so that a center axis of the optical path of the second light source light deflected by the optical deflection surface corresponds to a center axis of the optical path of the first light source light that has passed through the aperture,
   the first light source light and the second light source light entering the endoscope through the respective optical paths whose center axes correspond to each other; and
   the aperture of the optical path combiner is arranged at a light convergence point of the convergent light or in proximity thereof along the optical path of the first light source light such that an opening of the aperture is equal to or greater than a beam diameter of the first light source light at the distance from the light converger.

2. The endoscope light source apparatus according to claim 1, wherein the center axes of the optical paths of the first and second light source light correspond to an optical axis of an entrance end of the endoscope with the endoscope being connected to the endoscope light source apparatus.

3. The endoscope light source apparatus according to claim 2, wherein the first light source section further includes an optical fiber that guides the first light source light, and the first light source light is emitted from a position in proximity to the aperture or a position closer to the endoscope than the optical path combiner.

4. The endoscope light source apparatus according to claim 1, wherein a shape of the aperture is identical to a beam shape of the first light source light as projected onto a plane perpendicular to the center axis of the optical path of the first light source light.

5. The endoscope light source apparatus according to claim 1, the first light source section includes a laser light source, and the second light source section includes a lamp light source or a light emitting diode light source.

6. An endoscope apparatus comprising:
   the endoscope light source apparatus according to claim 1; and
   the endoscope to be connected to the endoscope light source apparatus,
   the endoscope including a light entrance section that takes in the first and second light source light, and a light guide that guides the first and second light source light that has entered the light entrance section.

7. The endoscope apparatus according to claim 6, wherein the light guide of the endoscope comprises a bundle fiber.

8. The endoscope apparatus according to claim 6, wherein the light guide of the endoscope comprises a single optical fiber.

* * * * *